(12) United States Patent
Robinson et al.

(10) Patent No.: US 9,122,156 B2
(45) Date of Patent: Sep. 1, 2015

(54) COMPOSITION OF MATTER AND MOLECULAR RESIST MADE THEREFROM

(71) Applicants: Alex Philip Graham Robinson, Birmingham (GB); Dongxu Yang, Selly Oak Birmingham (GB); Andreas Frommhold, Anger (DE); Thomas Lada, Somerville, MA (US); John L. Roth, Cohasset, MA (US); Xiang Xue, Winchester, MA (US); Edward A. Jackson, Franklin, MA (US)

(72) Inventors: Alex Philip Graham Robinson, Birmingham (GB); Dongxu Yang, Selly Oak Birmingham (GB); Andreas Frommhold, Anger (DE); Thomas Lada, Somerville, MA (US); John L. Roth, Cohasset, MA (US); Xiang Xue, Winchester, MA (US); Edward A. Jackson, Franklin, MA (US)

( * ) Notice: Subject to any disclaimer, the term of this patent is extended or adjusted under 35 U.S.C. 154(b) by 0 days.

(21) Appl. No.: 14/519,924

(22) Filed: Oct. 21, 2014

(65) Prior Publication Data

US 2015/0140491 A1 May 21, 2015

Related U.S. Application Data

(63) Continuation-in-part of application No. 14/068,254, filed on Oct. 31, 2013.

(51) Int. Cl.
*G03F 7/027* (2006.01)
*C07D 487/04* (2006.01)
*C07D 223/04* (2006.01)

(52) U.S. Cl.
CPC .............. *G03F 7/027* (2013.01); *C07D 223/04* (2013.01); *C07D 487/04* (2013.01)

(58) Field of Classification Search
CPC ..... G03F 7/004; C07D 487/04; C07D 223/04
USPC ........ 430/270.1; 540/484, 578, 567, 579, 470
See application file for complete search history.

(56) References Cited

U.S. PATENT DOCUMENTS

| 4,950,585 | A  | * | 8/1990  | Tachibana et al. | 430/385 |
| 7,838,438 | B2 | * | 11/2010 | Im et al.        | 438/778 |
| 8,062,429 | B2 | * | 11/2011 | Lee              | 134/1.3 |
| 8,173,584 | B2 | * | 5/2012  | Lee              | 510/175 |
| 2010/0105595 | A1 | * | 4/2010 | Lee              | 510/176 |

FOREIGN PATENT DOCUMENTS

WO    WO 2009058287 A1 *  5/2009

OTHER PUBLICATIONS

Lebedeva et al, "Tuning the interactions between electron spins in fulleren-based tried systems", Beilstein Journal of Organic Chemistry, 10, 332-343 (2014).*

* cited by examiner

*Primary Examiner* — Amanda C Walke
(74) *Attorney, Agent, or Firm* — The Patent Practice of Szmanda & Shelnut, LLC; Charles R. Szmanda; James G. Shelnut

(57) ABSTRACT

Disclosed herein is a composition of matter having a general structure chosen from (I), (II), (III) or (IV); at least one photo acid generator; at least one crosslinker; and at least one solvent;

-continued

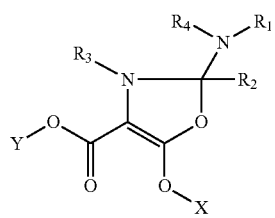 (II)

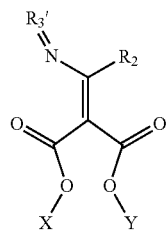 (III)

-continued

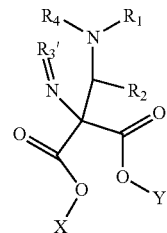 (IV)

wherein X and Y are the same or different, wherein at least one of X and Y comprises an acid labile group, wherein $R_1$ is a saturated or unsaturated group having from 1-4 carbon atoms, $R_2$ is chosen from hydrogen or a saturated or unsaturated group having from 1-4 carbon atoms, $R_3$ is a saturated or unsaturated group having from 1-4 carbon atoms, and $R_4$ is a saturated or unsaturated group having from 1-4 carbon atoms.

21 Claims, 5 Drawing Sheets

COMPOSITION OF MATTER AND MOLECULAR RESIST MADE THEREFROM

REFERENCE TO PRIOR FILED APPLICATIONS

The present application is a continuation-in-part, and claims the benefit under 35 U.S.C. §120, of U.S. patent application Ser. No. 14/068,254 filed on 14 Nov. 2012, entitled "Methanofullerenes," which application is incorporated by reference herein in its entirety.

FIELD OF THE INVENTION

The present application for patent is in the field of nanolithography materials and more specifically is in the field of molecular glass resists.

BACKGROUND

As is well known, the manufacturing process of various kinds of electronic or semiconductor devices such as ICs, LSIs and the like involves fine patterning of a resist layer on the surface of a substrate material such as a semiconductor silicon wafer. This fine patterning process has traditionally been conducted by the photolithographic method in which the substrate surface is uniformly coated with a positive or negative tone photosensitive composition to form a thin layer and selectively irradiating with actinic rays (such as ultraviolet (UV), deep UV, vacuum UV, extreme UV, x-rays, electron beams and ion beams) via a transmission or reflecting mask followed by a development treatment to selectively dissolve away the coated photosensitive layer in the areas exposed or unexposed, respectively, to the actinic rays leaving a patterned resist layer on the substrate surface. The patterned resist layer, thus obtained, may be utilized as a mask in the subsequent treatment on the substrate surface such as etching. The fabrication of structure with dimensions of the order of nanometers is an area of considerable interest since it enables the realization of electronic and optical devices which exploit novel phenomena such as quantum confinement effects and also allows greater component packing density. As a result, the resist pattern is required to have an ever increasing fineness which can be accomplished by using actinic rays having a shorter wavelength than the conventional ultraviolet light. Accordingly, it is now the case that, in place of the conventional ultraviolet light, electron beams (e-beams), excimer laser beams, EUV, BEUV and X-rays are used as the short wavelength actinic rays. Needless to say the minimum size obtainable is, in part, determined by the performance of the resist material and, in part, the wavelength of the actinic rays. Various materials have been proposed as suitable resist materials. For example, in the case of negative tone resists based on polymer crosslinking, there is an inherent resolution limit of about 10 nm, which is the approximate radius of a single polymer molecule.

It is also known to apply a technique called "chemical amplification" to resist materials. A chemically amplified resist material is generally a multi-component formulation in which there is a matrix material, frequently a main polymeric component, such as a polyhydroxystyrene (PHOST) resin protected by acid labile groups and a photo acid generator (PAG), as well as one or more additional components which impart desired properties to the resist. The matrix material contributes toward properties such as etching resistance and mechanical stability. By definition, the chemical amplification occurs through a catalytic process involving the PAG, which results in a single irradiation event causing the transformation of multiple resist molecules. The acid produced by the PAG reacts catalytically with the polymer to cause it to lose a functional group or, alternatively, cause a crosslinking event. The speed of the reaction can be driven, for example, by heating the resist film. In this way the sensitivity of the material to actinic radiation is greatly increased, as small numbers of irradiation events give rise to a large number of solubility changing events. As noted above, chemically amplified resists may be either positive or negative working.

Certain chemically amplified resists do not use large polymers. In cases where nanometer-scale patterning is desired, low molecular weight polymers or even small molecules may be used as the resist matrix material. These are sometimes referred to as "molecular glass" resists (MGRs), taken in this instance to include molecules such as oligomers, polyaromatic hydrocarbon derivatives, discotic liquids crystals, fullerenes, macrocycles, small amorphous, and other low molecular weight resists. Although MGRs may offer many potential advantages over polymeric chemically amplified resists, there are still some things about this class of materials that could potentially pose challenges. Removal and subsequent volatilization of protecting groups in positive tone molecular resists may cause a loss of up to approximately 50% of the mass of the resist, potentially leading to a loss of pattern quality. The small sizes of molecular resist compounds, and often correspondingly low glass transition temperatures, can also restore material integrity but may compromise pattern quality.

Accordingly, there is a need for improved negative molecular glass resists. It is to the provision and characterization of such molecular glass resists that the various embodiments of the present written description are directed.

DETAILED DESCRIPTION OF THE DRAWINGS

Figure 1:
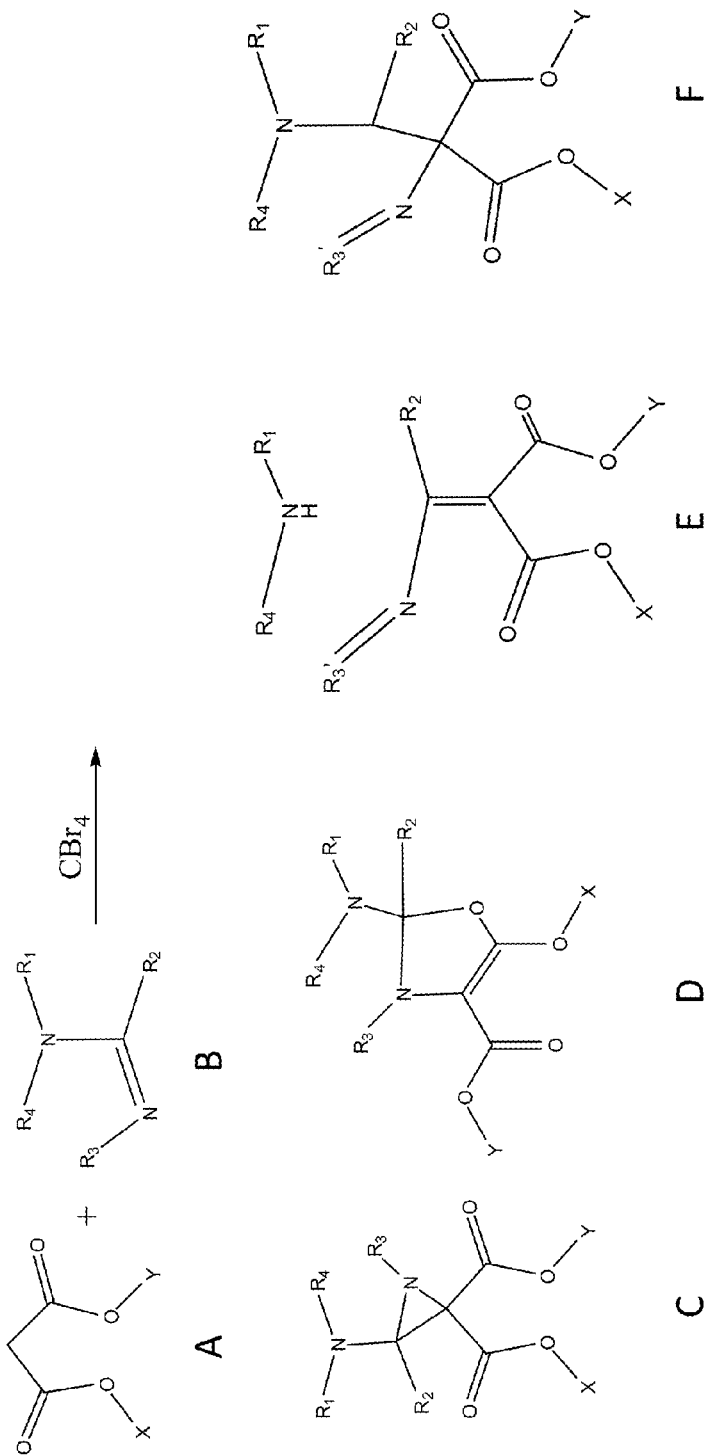
FIG. 1 illustrates the general reaction of an imidamide with a malonate ester in the presence of a bromine donor such as $CBr_4$ as disclosed herein.

FIG. 1 illustrates the general reaction of an imidamide with a malonate ester, in the presence of a bromine donor such as $CBr_4$ as disclosed herein. The malonate ester, A, reacts with the imidamide, B, in the presence of $CBr_4$ to yield possible products C, D, E and F that are believed to be energetically accessible under certain reaction conditions.

Figure 2:
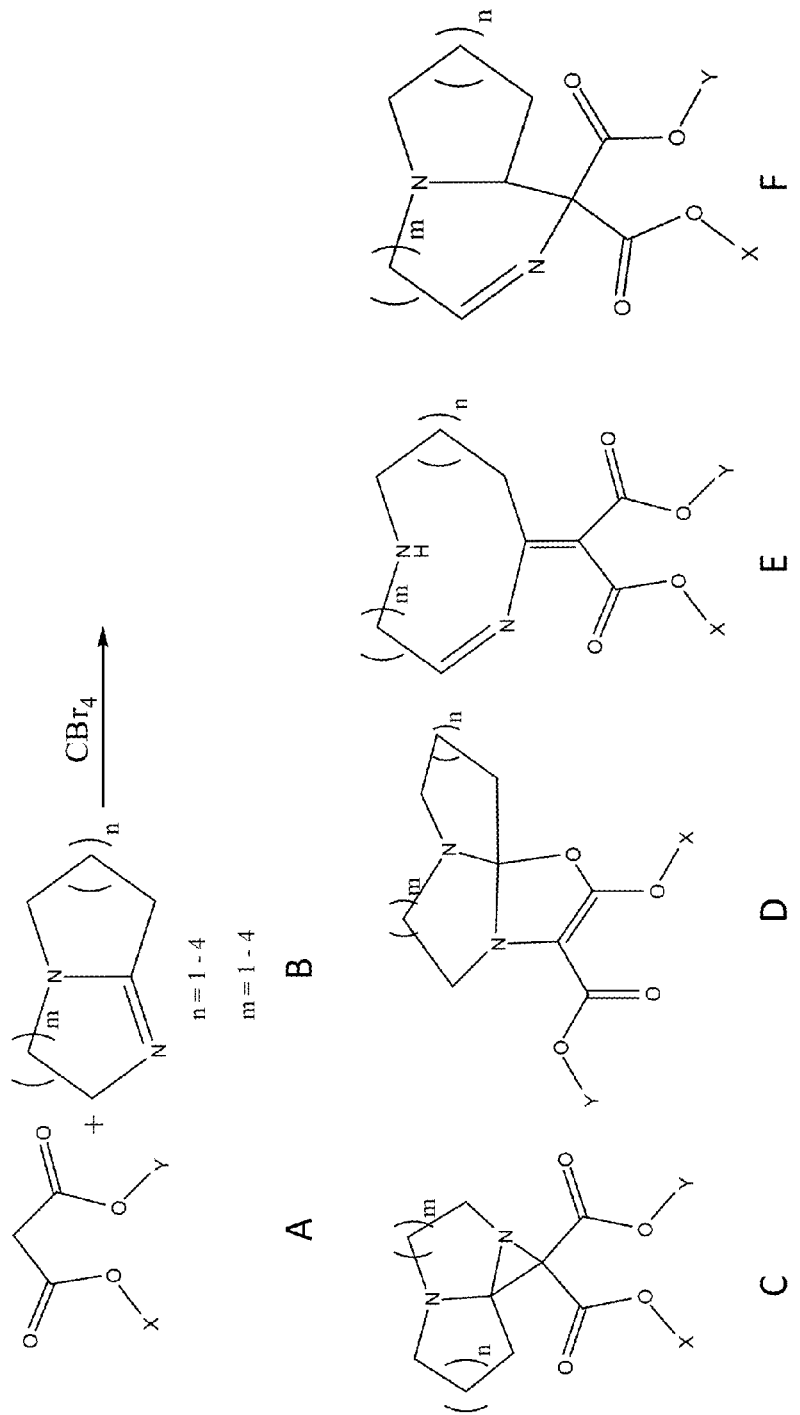
FIG. 2 illustrates the reaction of a fused ring imidamide with a malonate ester, in the presence of a bromine donor such as $CBr_4$ as disclosed herein.

FIG. 2 illustrates the general reaction of a fused ring imidamide with a malonate ester, in the presence of a bromine donor such as $CBr_4$ as disclosed herein. The malonate ester, A, reacts with the fused ring imidamide, B, in the presence of $CBr_4$ to yield possible products C, D, E and F that are believed to be energetically accessible under certain reaction conditions.

Figure 3:
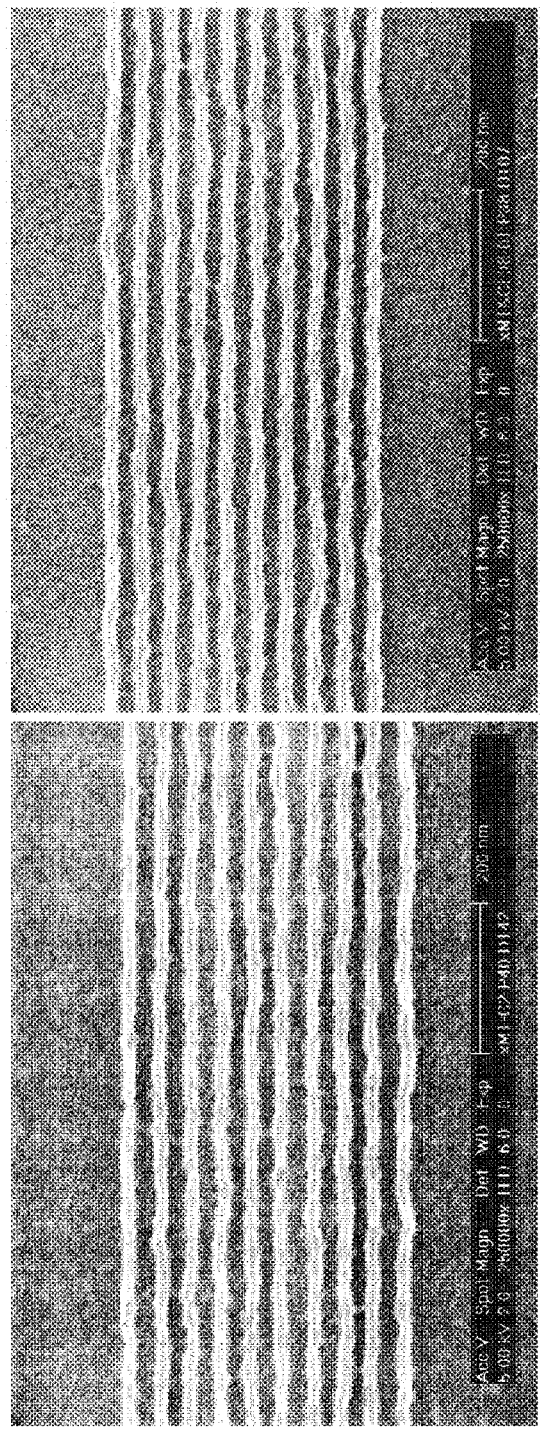
FIG. 3 shows the lithographic features produced using Composition Example 3 and Composition Example 4, described infra.
Figure 4:
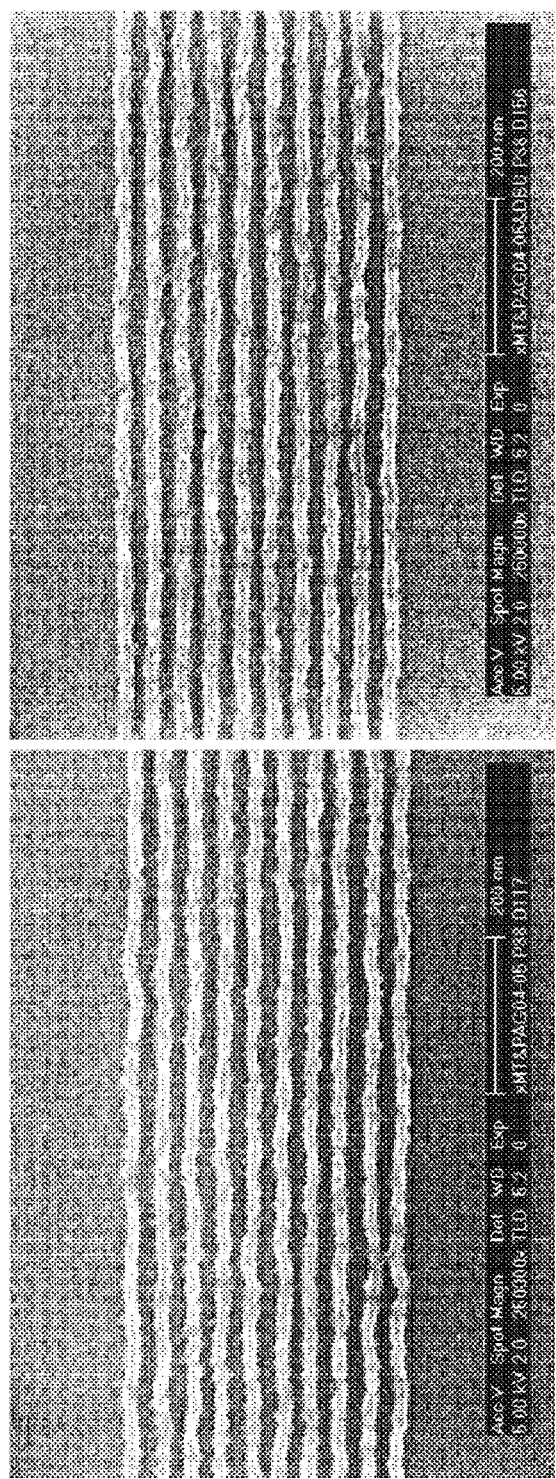
FIG. 4 shows the lithographic features produced using Composition Example 5 and Composition Example 6, described infra.
Figure 5:
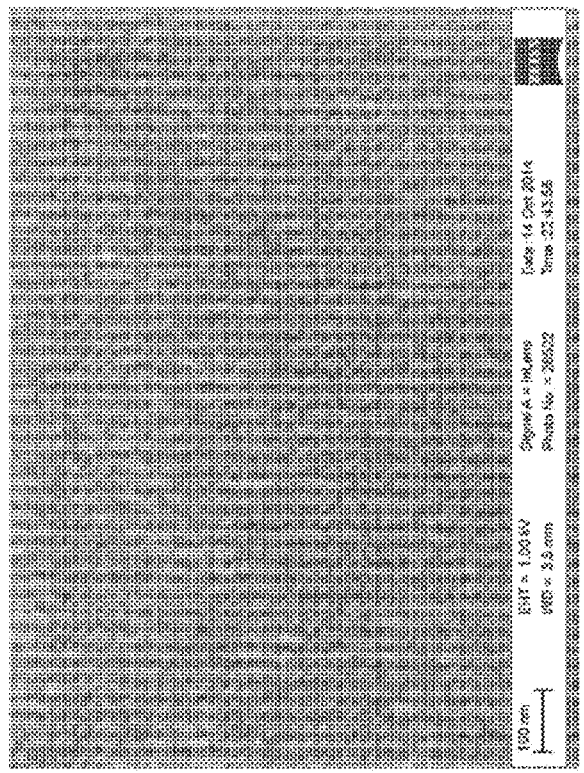
FIG. 5 shows the lithographic features produced using Composition Example 7, described infra.

FIG. 3 shows a scanning electron micrograph of the lithographic features produced using Composition Example 3 (FIG. 3(A)), and Composition Example 4 (FIG. 3(B)), described infra FIG. 4 shows a scanning electron micrograph of the lithographic features produced using Composition Example 5 (FIG. 4(A)), and Composition Example 6 (FIG. 4(B)), described infra FIG. 5 shows a scanning electron micrograph of the lithographic features produced using Composition Example 7, described infra.

DETAILED DESCRIPTION

As used herein, the conjunction "and" is intended to be inclusive and the conjunction "or" is not intended to be exclusive unless otherwise indicated or required by the context. For example, the phrase "or, alternatively" is intended to be exclusive. As used herein, the term "exemplary" is intended to describe an example and is not intended to indicate preference. As used herein, the term "energetically accessible" is used to describe products that may be thermodynamically or kinetically available via a chemical reaction.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise. Unless otherwise required by the context, chemical substitution material in parentheses indicates that the substitution may or may not be present. Thus, for example "(perfluoro) octanesulfinate" may or may not include perfluorination.

Disclosed herein is a negative working, photosensitive composition comprising an ester, wherein the ester is a product of a chemical reaction between a malonate ester and an imidamide in the presence of a suitable halogen donor or pseudohalogen donor; at least one crosslinkable material; and at least one acid generator,

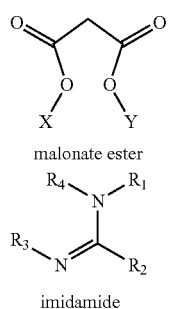

malonate ester imidamide wherein X and Y are the same or different, wherein at least one of X and Y comprises an acid labile group, wherein $R_1$ is a saturated or unsaturated group having from 1-4 carbon atoms, $R_2$ is chosen from hydrogen or a saturated or unsaturated group having from 1-4 carbon atoms, $R_3$ is a saturated or unsaturated group having from 1-4 carbon atoms, and $R_4$ is a saturated or unsaturated group having from 1-4 carbon atoms.

Further disclosed herein is a negative working, photosensitive composition comprising an ester produced by the above chemical reaction; at least one crosslinkable material; and at least one acid generator, wherein, in the imidamide, $R_2$ is a saturated or unsaturated group having from 1-4 carbon atoms, $R_1$ and $R_2$ are conjoined by a chemical bond to form a ring structure having 5-8 members, and wherein, in the imidamide, $R_3$ and $R_4$ are conjoined by a chemical bond to form a ring structure having 5-8 members.

Still further disclosed herein is a negative working photosensitive composition, wherein the imidamide comprises a fused ring structure as shown:

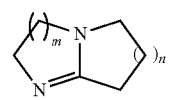

wherein m=1-4 and n=1-4.

Disclosed herein is a negative working photosensitive composition comprising: at least one ester, having a structure chosen from (I), (II), (III) or (IV); at least one photo acid generator; at least one crosslinker; and at least one solvent; wherein X and Y are the same or different, wherein at least one of X and Y comprises an acid labile group, wherein R1 is a saturated or unsaturated group having from 1-4 carbon atoms, R2 is chosen from hydrogen or a saturated or unsaturated group having from 1-4 carbon atoms, R3 is a saturated or unsaturated group having from 1-4 carbon atoms, and R4 is a saturated or unsaturated group having from 1-4 carbon atoms.

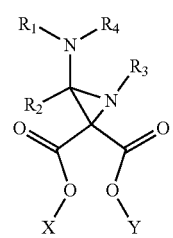

(I)

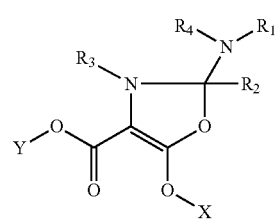

(II)

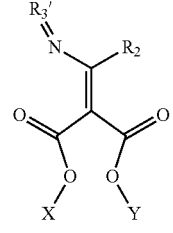

(III)

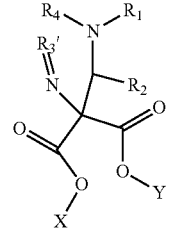

(IV)

In the above, the group —N=$R_3$' is used here to denote the ylidene amine, produced starting with the group $R_3$, where permitted by the chemical substitution.

Further disclosed herein is a negative working composition comprising an ester, having a structure chosen from (I), (II), (III), or (IV); at least one photo acid generator; and at least one crosslinker; wherein $R_2$ is a saturated or unsaturated group having from 1-4 carbon atoms, $R_1$ and $R_2$ are conjoined by a chemical bond to form a ring structure having 5-8 members, and wherein $R_3$ and $R_4$ are conjoined by a chemical bond to form a ring structure having 5-8 members, where appropriate.

Disclosed herein is negative working composition of matter comprising an ester having a structure chosen from (V), (VI), (VII), or (VIII); at least one photo acid generator; at least one crosslinker; and, optionally, at least one solvent; wherein X and Y are the same or different, and wherein at least one of X and Y comprises an acid labile group and wherein m=1-4 and wherein n=1-4.

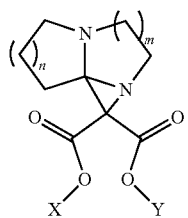

(V)

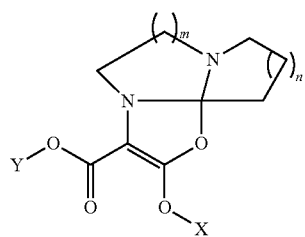

(VI)

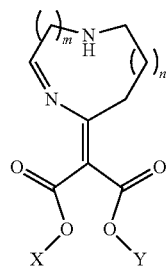

(VII)

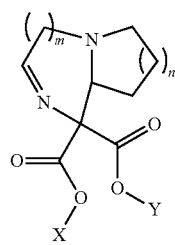

(VIII)

In all of the above embodiments, the acid generator may be a photoacid generator. Thus, negative working photosensitive compositions are obtained.

In the above disclosed structures, at least one of X or Y may comprise an acid labile group, such that X or Y has the general structure

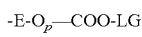

which may or may not comprise an extender chain, -E-. In addition, the acid labile group may comprise a carbonate (for which p=1) or a carboxylate (for which p=0), and a leaving group, LG. In the case of the carbonate esters, both the leaving group and $CO_2$ are eliminated during the deprotection reaction, leaving behind an OH group. In the case of the carboxylate esters, the leaving group is eliminated, leaving behind a carboxylic acid. In certain circumstances, the carboxylic acid may be eliminated via decarboxilation using a base. As an example, either or both of X and Y may comprise a structure such as -alkyl-aryl-(O)$_p$—COO-LG wherein p=0 or 1, wherein the portion, -alkyl-aryl- is an extender chain, wherein alkyl is a branched or unbranched, substituted or unsubstituted divalent alkyl chain of 1-16 carbon atoms having 0-16 heteroatoms substituted into the chain, aryl is a substituted or unsubstituted divalent phenyl group, divalent heteroaromatic group, or divalent fused aromatic or fused heteroaromatic group, wherein —O—COO-LG is an acid labile group and wherein LG is a leaving group. In addition to the carbonate ester, depicted above, the acid labile group may comprise an acid labile carboxylic acid ester having similar leaving groups, LG. The acid labile group may be a a tert-butoxycarbonate group, a tert-butoxy carboxylate group or other carbonate or carboxylate ester having a leaving group such as, without limitation, a tertiary alkyl or cycloalkyl group, an allicyclic group, a ketal or cyclic aliphatic ketal, or an acetal. In addition, the acid labile group may comprise a mass persistent moiety in which p=0 and the leaving group is bonded to the extender chain. Non limiting examples may generally be represented by the structure

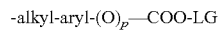

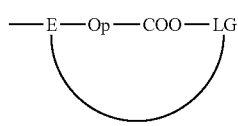

and may, for example, include the following:

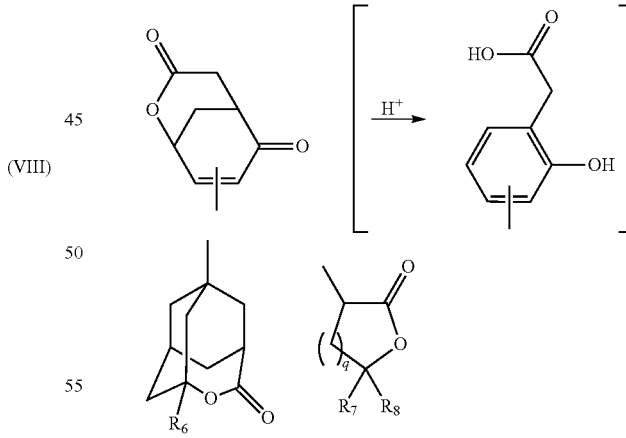

wherein the matter in brackets, supra, shows the presumed acidolysis reaction, wherein the points of attachment to the remainder of the group, E, are shown. Wherein $R_6$ is a hydrogen, methyl, ethyl, or benzyl group, $R_7$ and $R_8$ may be the same or different and may be methyl, ethyl, or benzyl groups and q=0 to 4. Examples of mass persistent resists are known. See, for example, Klop et al., Chem. Commun., (2002), 2956-2957, and Ushirogouchi et al., Proc. SPIE, 3999, 1147, (2000).

In addition, X and Y may comprise, for example, without limitation, no extender chain, or divalent extender chains comprising -alkyl-, -aryl-, -alkyl-aryl-, -aryl-alkyl-, -alkoxy-, -alkoxy-aryl-, -aryl-alkoxy-, -alkyl-alkoxy-, -alkoxy-alkyl-, or combinations of the foregoing More specifically, the -alkyl- group, above, can be a branched or unbranched divalent alkyl chain of 1-16 carbons with or without heteroatoms substituted into the chain, such as, for example, —CH2-, —CH2CH2-, —CH(CH3)CH2-, —CH2CH2CH2-, —CH2CH2CH2CH2-, butylene isomers, and the higher analogs up to and including hexadecylene, as well as their isomers. As used herein -alkyl- also includes any unsaturations in the chain such an olefin group, such as for example, —CH=CH—, or an alkynyl group. As mentioned the -alkyl- group may have heteroatoms substituted into the chain as part or the chain, such as O, N, S, S=O or SO2 and the like, such as, for example, —(CH2CH2-O)$_z$- wherein z is between about 1 and about 16, or —(CH2CH2NH)$_w$- wherein w is between about 1 and about 16, and the like. In accordance with the description above, the group, -alkoxy- may comprise one or more branched or unbranched alkyl groups such as -ethoxy-, -propoxy- or -isopropoxy- groups, separated by oxygen atoms. Also included are branched alkyl groups that contain heteroatoms in the ring, such as, for example —(CH2CH2NR")v- wherein R" can be a branched or unbranched divalent alkyl chain of 1-16 carbons with or without heteroatoms substituted into the R" chain.

-Aryl-, above, is a substituted or unsubstituted divalent aromatic group, such aromatic groups include, for example the phenylenes (—C6H4-), the fused divalent aromatic group, such as, for example, the naphthylenes (—C10H6-), the anthacenylenes (—C14H8-) and the like, as well as the heteroaromatic groups, such as, for example, the nitrogen heterocycles: pyridines, quinolines, pyrroles, indoles, pyrazoles, the triazines, and other nitrogen-containing aromatic heterocycles well known in the arts, as well as the oxygen heterocycles: furans, oxazoles and other oxygen-containing aromatic heterocycles, as well the sulfur containing aromatic heterocycles, such as, for example, thiophenes.

Turning to the leaving groups, LG, on one of X or Y, LG may be H or D as long as the other of X or Y comprises an acid labile group. Leaving groups are taken to be those groups that may be removed or are removable by acidolysis, and may include, for example and without limitation, tertiary alkyl leaving groups, which have the general structure —CR$_5$R$_6$R$_7$, wherein R$_5$, R6, and R7 may be the same or different and represent linear or branched alkyl, heteroalkyl or alkyl aryl groups. Without limitation, exemplary groups may be a tert-butyl group, a tert-pentyl group, a 2,3-dimethylbutan-2-yl group, a 2,3,3-trimethylbutan-2-yl group, a 2,3-dimethylpentan-3-yl group, a 2-methylbicyclo[2.2.1]heptan-2-yl group, a bicyclo[2.2.1]heptan-2-yl group, a 1-methylcyclopentyl group, a 1-ethylcyclopentyl group, a 1-methylcyclohexyl group, a 1-ethylcyclohexyl group, a 2-methyladamantyl group or a 2-ethyladamantyl group. Further, exemplary tertiary carbon containing leaving groups may include ring structures having oxygen atoms such as a mevalonic lactone-yl group.

Leaving groups may also include, without limitation, ketals. Exemplary ketals include, without limitation, methoxycyclopropanyl, ethoxycyclopropanyl, butoxycyclohexanyl, methoxycyclobutanyl, ethoxycyclobutanyl, methoxycyclopentanyl, ethoxycyclopentanyl, methoxycyclohexanyl, ethoxycyclohexanyl, propoxycyclohexanyl, methoxycycloheptanyl, methoxycyclooctanyl or methoxyadamantyl.

Leaving groups may also include acetals. Acetals may be derived from known reactions with vinyl ethers to produce esterified leaving groups, such as alkoxyalkyl esters. Vinyl ethers that may be used for this purpose include methyl vinyl ether, ethyl vinyl ether, butyl vinyl ether, cyclohexyl vinyl ether, 2-phenoxyethyl vinyl ether, phenyl vinyl ether, and p-methoxyphenyl vinyl ether.

In addition, LG may be, for example, substituted methyl groups, 1-substituted ethyl groups, 1-substituted alkyl groups, silyl groups, germyl groups, alkoxycarbonyl group, acyl groups and cyclic acid-dissociable groups. The substituted methyl groups include, for example, the methoxymethyl group, methylthiomethyl group, ethoxy methyl group, ethylthiomethyl group, methoxyethoxy methyl group, benzyloxymethyl group, benzylthiomethyl group, phenacyl group, bromophenacyl group, methoxyphenacyl group, methylthiophenacyl group, α-methylphenacyl group, cyclopropylmethyl group, benzyl group, diphenyl methyl group, triphenylmethyl group, bromobenzyl group, nitrobenzyl group, methoxybenzyl group, methylthiobenzyl group, ethoxy benzyl group, ethylthiobenzyl group, piperonyl group, methoxycarbonylmethyl group, ethoxy carbonylmethyl group, N-propoxy carbonylmethyl group, isopropoxy carbonylmethyl group, N-butoxycarbonylmethyl group and t-butoxycarbonylmethyl group. The 1-substituted ethyl groups include, for example. 1-methoxyethyl group, 1-methylthioethyl group, 1,1-dimethoxyethyl group, 1-ethoxy ethyl group, 1-ethylthioethyl group, 1,1-diethoxy ethyl group, 1-phenoxyethyl group, 1-phenylthioethyl group, 1,1-diphenoxyethyl group, 1-benzyloxyethyl group, 1-benzylthioethyl group, 1-cyclopropylethyl group, 1-phenylethyl group, 1,1-diphenyl ethyl group, 1-methoxycarbonylethyl group, 1-ethoxy carbonylethyl group, 1-N-propoxy carbonylethyl group, 1-isopropoxy carbonylethyl group, 1-N-butoxycarbonylethyl group and the 1-t-butoxycarbonylethyl group. The 1-substituted alkyl group include the isopropyl group, sec-butyl group, t-butyl group, 1,1-dimethylpropyl group, 1-methylbutyl group and 1,1-dimethylbutyl group.

The silyl acid leaving groups include, for example, the trimethyl silyl group, ethyldimethylsilyl group, methyldiethylsilyl group, triethylsilyl group, isopropyldimethylsilyl group, methyldiisopropylsilyl group, triisopropylsilyl group, t-butyldimethylsilyl group, methyldi-t-butylsilyl group, tri-t-butylsilyl group, phenyldimethylsilyl group, methyldiphenyl silyl group and triphenylsilyl group. The germyl groups include, for example, the trimethyl germyl group, ethyldimethylgermyl group, methyldiethylgermyl group, triethylgermyl group, isopropyldimethylgermyl group, methyldiisopropylgermyl group, triisopropylgermyl group, t-butyldimethylgermyl group, methyldi-t-butylgermyl group, tri-t-butylgermyl group, phenyldimethylgermyl group, methyldiphenyl germyl group and triphenylgermyl group.

The alkoxycarbonyl leaving groups include the methoxycarbonyl group, ethoxy carbonyl group, isopropoxy carbonyl group and t-butoxycarbonyl group. The acyl acid labile groups include, for example, the acetyl group, propionyl group, butyryl group, heptanoyl group, hexanoyl group, valeryl group, pivaloyl group, isovaleryl group, lauroyl group, myristoyl group, palmitoyl group, stearoyl group, oxaryl group, malonyl group, succinyl group, glutaryl group, adipoyl group, piperoyl group, suberoyl group, azelaoyl group, sebacoyl group, acrylyl group, propioloyl group, methacryloyl group, crotonoyl group, oleoyl group, maleoyl group, fumaroyl group, mesaconoyl group, camphoroyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluene sulfonyl group and the mesyl group.

Leaving groups may also include ring or alicyclic structures that may be removed by acidolysis such as, for example, a cyclopropyl group, cyclopentyl group, cyclohexyl group, cyclohexanyl group, 4-methoxycyclohexyl group, tetrahydropyranyl group, tetrahydrofuranyl group, tetrahydrothiopyranyl group, tetrahydrothiofuranyl group, 3-bromo tetrahydropyranyl group, 4-methoxy tetrahydropyranyl group, 4-methoxy tetrahydrothiopyranyl group and 3-tetrahydrothiophene-1,1-dioxy group.

Without intending to be bound by theory, it is believed that the $CBr_4$ functions in the coupling reactions of FIGS. 1 and 2 as a bromonium, halonium or pseudo halonium source in the reaction to substitute for one of the hydrogen atoms on the central malonate carbon atom. Suitable replacements for $CBr_4$ may be $CCl_4$, $I_2$, $Br_2$, an aryl cyanate such as phenyl cyanate, cyanogen, or N-bromosuccinimide.

Negative working photosensitive compositions, disclosed herein comprise an ester such as (I)-(VIII), described above, or any other product resulting from the reaction between a malonate ester, described above, and an imidamide, described above, in the presence of a suitable halogen donor or pseudohalogen donor; at least one crosslinkable material; and at least one acid generator, wherein the ester takes the place of at least a portion of the resin used in conventional negative working photoresists.

The above described negative working photosensitive compositions further comprise, in admixture, photoacid generators. Without limitation, these may include onium salt compounds, such as sulfonium salts, phosphonium salts or iodonium salts, sulfone imide compounds, halogen-containing compounds, sulfone compounds, ester sulfonate compounds, quinone diazide compounds, diazomethane compounds, dicarboximidyl sulfonic acid esters, ylideneaminooxy sulfonic acid esters, sulfanyldiazomethanes, or a combination thereof.

Specific examples of photoacid generators include include diphenyl(4-phenylthiophenyl)sulphonium hexafluoroantimonate, 4,4'-bis[diphenylsulfoniolphenylsulphide bis hexafluoroantimonate and combinations there of, triphenylsulfonium nonafluorobutanesulfonate, triphenylsulfonium trifluoromethanesulfonate, triphenylsulfonium pyrenesulfonate, triphenylsulfonium dodecylbenzenesulfonate, triphenylsulfonium p-toluene sulfonate, triphenylsulfonium benzenesulfonate, triphenylsulfonium 10-camphor-sulfonate, triphenylsulfonium(perfluoro)octanesulfonate, triphenylsulfonium 2-trifluoromethyl benzenesulfonate, triphenylsulfonium hexafluoroantimonate, triarylsulfonium hexafluoroantimonates, the triarylsulfonium hexafluorophosphates, the triarylsulfonium tetrafluoroborates as well as other tetrafluoroborates, triphenylsulfonium napthalenesulfonate, tri(4-hydroxyphenyl)sulfonium nonafluorobutanesulfonate, tri(4-hydroxyphenyl)sulfoniumtrifluoromethanesulfonate, tri(4-hydroxyphenyl)sulfonium pyrenesulfonate, tri(4-hydroxyphenyl)sulfoniumdodecylbenzenesulfonate, tri(4-hydroxyphenyl)sulfonium p-toluene sulfonate, tri(4-hydroxyphenyl)sulfonium benzenesulfonate, tri(4-hydroxyphenyl)sulfonium10-camphor-sulfonate, tri(4-hydroxyphenyl)sulfonium(perfluoro)octanesulfonate, tri(4-hydroxyphenyl)sulfonium 2-trifluoromethylbenzenesulfonate, tri(4-hydroxyphenyl)sulfonium hexafluoroantimonate, tri(4-hydroxyphenyl)sulfonium napthalenesulfonate, diphenyliodonium nonafluorobutanesulfonate, diphenyliodonium trifluoromethanesulfonate, diphenyliodonium pyrenesulfonate, diphenyliodonium dodecylbenzenesulfonate, diphenyliodonium p-toluene sulfonate, diphenyliodonium benzenesulfonate, diphenyliodonium 10-camphor-sulfonate, diphenyliodonium(perfluoro)octanesulfonate, diphenyliodonium 2-trifluoromethylbenzenesulfonate, bis(4-t-butylphenyl)iodonium nonafluorobutanesulfonate, bis(4-t-butylphenyl)iodonium trifluoromethanesulfonate, bis(4-t-butylphenyl)iodonium pyrenesulfonate, bis(4-t-butylphenyl)iodonium dodecylbenzenesulfonate, bis(4-t-butylphenyl)iodonium p-toluene sulfonate, bis(4-t-butylphenyl)iodonium benzenesulfonate, bis(4-t-butylphenyl)iodonium 10-camphor-sulfonate, bis(4-t-butylphenyl)iodonium(perfluoro)octanesulfonate, bis(4-t-butylphenyl)iodonium 2-trifluoromethylbenzenesulfonate, 4-hydroxy-1-naphthyl tetrahydrothiophenium trifluoromethanesulfonate and 4,7-dihydroxy-1-naphthyl tetrahydrothiophenium trifluoromethanesulfonate.

Specific examples of a sulfone imide compound include N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hepto-5-ene-2,3-dicarboxyimide, N-(trifluoromethylsulfonyloxy)-7-oxabicyclo[2.2.1]hepto-5-ene-2,3-dicarboxyimide, N-(trifluoromethylsulfonyloxy)bicyclo[2.2.1]heptane-5,6-oxy-2,3-dicarboxyimide, N-(trifluoromethylsulfonyloxy)naphthylimide, N-(10-camphor-sulfonyloxy)succinimide, N-(10-camphor-sulfonyloxy)phthalimide, N-(10-camphor-sulfonyloxy)diphenyl maleimide, N-(10-camphor-sulfonyloxy)bicyclo[2.2.1]hepto-5-ene-2,3-dicarboxyimide, N-(10-camphor-sulfonyloxy)-7-oxabicyclo[2.2.1]hepto-5-ene-2,3-dicarboxyimide, N-(10-camphor-sulfonyloxy)bicyclo[2.2.1]heptane-5,6-oxy-2,3-dicarboxyimide, N-(10-camphor-sulfonyloxy)naphthylimide, N-(p-toluene sulfonyloxy)succinimide, N-(p-toluene sulfonyloxy)phthalimide, N-(p-toluene sulfonyloxy)diphenyl maleimide, N-(p-toluene sulfonyloxy)bicyclo[2.2.1]hepto-5-ene-2,3-dicarboxyimide, N-(p-toluene sulfonyloxy)-7-oxabicyclo[2.2.1]hepto-5-ene-2,3-dicarboxyimide, N-(p-toluene sulfonyloxy)bicyclo[2.2.1]heptane-5,6-oxy-2,3-dicarboxyimide, N-(p-toluene sulfonyloxy)naphthylimide, N-(2-trifluoromethylbenzenesulfonyloxy)succinimide, N-(2-trifluoromethylbenzenesulfonyloxy)phthalimide, N-(2-trifluoromethylbenzenesulfonyloxy)diphenyl maleimide, N-(2-trifluoromethylbenzenesulfonyloxy)bicyclo[2.2.1]hepto-5-ene-2,3-dicarboxyimide, N-(2-trifluoromethylbenzenesulfonyloxy)-7-oxabicyclo[2.2.1]hepto-5-ene-2,3-dicarboxyimide, N-(2-trifluoromethylbenzenesulfonyloxy)bicyclo[2.2.1]heptane-5,6-oxy-2,3-dicarboxyimide, N-(2-trifluoromethylbenzenesulfonyloxy)naphthylimide, N-(4-fluorobenzenesulfonyloxy)succinimide, N-(4-fluorobenzenesulfonyloxy)phthalimide, N-(4-fluorobenzenesulfonyloxy)diphenyl maleimide, N-(4-fluorobenzenesulfonyloxy)bicyclo[2.2.1]hepto-5-ene-2,3-dicarboxyimide, N-(4-fluorobenzenesulfonyloxy)-7-oxabicyclo[2.2.1]hepto-5-ene-2,3-dicarboxyimide, N-(4-fluorobenzenesulfonyloxy)bicyclo[2.2.1]heptane-5,6-oxy-2,3-dicarboxyimide, N-(4-fluorobenzenesulfonyloxy)naphthylimide, N-(nonafluorobutylsulfonyloxy)succinimide, N-(nonafluorobutylsulfonyloxy)phthalimide, N-(nonafluorobutylsulfonyloxy)diphenyl maleimide, N-(nonafluorobutylsulfonyloxy)bicyclo[2.2.1]hepto-5-ene-2,3-dicarboxyimide, N-(nonafluorobutylsulfonyloxy)-7-oxabicyclo[2.2.1]hepto-5-ene-2,3-dicarboxyimide, N-(nonafluorobutylsulfonyloxy)bicyclo[2.2.1]heptane-5,6-oxy-2,3-dicarboxyimide and N-(nonafluorobutylsulfonyloxy)naphthylimide.

Examples of halogen-containing compounds include, for example, haloalkyl group-containing hydrocarbon compounds and haloalkyl group-containing heterocyclic compounds. Specific examples of halogen-containing compounds include (poly)trichloromethyl-s-triadine derivatives such as phenyl-bis(trichloromethyl)-s-triadine, 4-methoxyphenyl-bis(trichloromethyl)-s-triadine and 1-naphthyl-bis(trichloromethyl)-s-triadine, and 1,1-bis(4-chlorophenyl)-2,2,2-trichloroethane.

Examples of sulfone compounds include, for example, β-ketosulfone and β-sulfonylsulfone, and the α-diazo compounds thereof. Specific examples of the sulfone compounds include phenacyl phenylsulfone, mesitylphenacyl sulfone, bis(phenylsulfonyl)methane, 1,1-bis(phenylsulfonyl)cyclobutane, 1,1-bis(phenylsulfonyl)cyclopentane, 1,1-bis(phenylsulfonyl)cyclo hexane, and 4-trisphenacyl sulfone.

Examples of sulfonate ester compounds include alkylsulfonate esters, haloalkyl sulfonate esters, aryl sulfonate esters sand imino sulfonates. Specific examples of sulfonate ester compounds include benzoin tosylate, pyrogallol tristrifluoromethanesulfonate, pyrogallol trisnonafluorobutanesulfonate, pyrogallol(perfluoro)methanesulfonate triester, nitrobenzyl-9,10-diethoxy anthracene-2-sulfonate, α-methylol benzoin tosylate, α-methylol benzoin(perfluoro)octanesulfonate, α-methylol benzoin trifluoromethanesulfonate and α-methylol benzoin dodecylsulfonate.

Examples of quinone diazide compounds include compounds containing a 1,2-quinone diazide sulfonyl group such as the 1,2-benzoquinone diazide-4-sulfonyl group, 1,2-naphthoquinone diazide-4-sulfonyl group, 1,2-naphtho quinine diazide-5-sulfonyl group and 1,2-naphthoquinone diazide-6-sulfonyl group. Specific examples of quinone diazide compounds include 1,2-quinone diazidesulfonate esters of (poly)hydroxyphenylaryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 3'-methoxy-2,3,4,4'-tetrahydroxybenzophenone, 2,2',4,4'-tetrahydroxybenzophenone, 2,2'3,4,4'-pentahydroxybenzophenone, 2,2'3,4,6'-pentahydroxybenzophenone, 2,3,3'4,4',5'-hexahydroxybenzophenone, 2,3'4,4',5',6-hexahydroxybenzophenone; 1,2-quinone diazide sulfonate esters of bis[(poly)hydroxyphenyl]alkanes such as bis(4-hydroxyphenyl)methane, bis(2,4-dihydroxyphenyl)methane, bis(2,3,4-trihydroxyphenyl)methane, 2,2-bis(4-hydroxyphenyl)propane, 2,2-bis(2,4-dihydroxyphenyl)propane and 2,2-bis(2,3,4-trihydroxyphenyl)propane; 1,2-quinone diazide sulfonate esters of (poly)hydroxytriphenylalkanes such as 4,4'-dihydroxytriphenylmethane, 4,4',4''-trihydroxytriphenylmethane, 2,2',5,5'-tetramethyl-2'',4,4'-trihydroxytriphenylmethane, 3,3',5,5'-tetramethyl-2'',4,4'-trihydroxytriphenylmethane, 4,4',5,5'-tetramethyl-2,2',2''-trihydroxytriphenylmethane, 2,2',5,5'-tetramethyl-4,4',4''-trihydroxytriphenylmethane, 1,1,1-tris(4-hydroxyphenyl)ethane, 1,1-bis(4-hydroxyphenyl)-1-phenylethane, 1,1-bis(4-hydroxyphenyl)-1-[4-{1-(4-hydroxyphenyl)-1-methylethyl}phenyl]ethane, 1,1,3-tris(2,5-dimethyl-4-hydroxyphenyl)propane, 1,1,3-tris(2,5-dimethyl-4-hydroxyphenyl)butane and 1,3,3-tris(2,5-dimethyl-4-hydroxyphenyl)butane; and 1,2-quinone diazide sulfonate esters of (poly)hydroxyphenylflavans such as 2,4,4-trimethyl-2',4',7-trihydroxy-2-phenylflavan and 2,4,4-trimethyl-2',4',5',6',7-pentahydroxy-2-phenylflavan.

Specific examples of diazomethane compounds include bis(trifluoromethylsulfonyl)diazomethane, bis(cyclohexylsulfonyl)diazomethane, bis(phenylsulfonyl)diazomethane, bis(p-toluene sulfonyl)diazomethane, methylsulfonyl-p-toluene sulfonyldiazomethane, 1-cyclohexylsulfonyl-1-(1,1-dimethylethylsulfonyl)diazomethane and bis(1,1-dimethylethylsulfonyl)diazomethane.

Negative working materials may also comprise a crosslinker. Crosslinkers, suitable for the current disclosure, comprise compounds able to cross-link with the above disclosed ester, after it is deprotected, but, in any case, if either X or Y comprise functional groups that can be reacted with the crosslinker. Among these reactive functional groups are alcohols, phenols, protic amides, carboxylic acids and the like. Before the deprotection reaction occurs, at least a portion of the reactive functional groups are protected by an acid labile group described above. Once the deprotection reaction occurs, the crosslinker may react with the deprotected functional group. Not to be held to theory, it is believed that the photogenerated acid not only reacts with the acid-labile group of the above disclosed ester but aids in the reaction of the crosslinker with itself and the ester. Examples of crosslinkers include compounds comprising at least one type of substituted group that possess a cross-linking reactivity with the phenol or similar group of the on the deprotected ester. Specific examples of this crosslinking group include, without limitation, the glycidyl ether group, the oxetane group, glycidyl ester group, glycidyl amino group, methoxymethyl group, ethoxy methyl group, benzyloxymethyl group, dimethylamino methyl group, diethylamino methyl group, dimethylol amino methyl group, diethylol amino methyl group, morpholino methyl group, acetoxymethyl group, benzyloxy methyl group, formyl group, acetyl group, vinyl group and isopropenyl group.

Non limiting examples of compounds having the aforementioned cross-linking substituted group include, bisphenol A-based epoxy compounds, bisphenol F-based epoxy compounds, bisphenol S-based epoxy compounds, novolac resin-based epoxy compound, resol resin-based epoxy compounds, poly(hydroxystyrene)-based epoxy compounds, (3-ethyloxetan-3-yl)methanol, 1,3-bis(((3-ethyloxetan-3-yl)methoxy)methyl)benzene, 3,3'-oxybis(methylene)bis(3-ethyloxetane), and phenol novolak oxetane, sold by Toagosei America Inc. of West Jefferson, Ohio, as OXT-101, OXT-121, OXT-221 and PNOX1009, respectively, methylol group-containing melamine compounds, methylol group-containing benzoguanamine compounds, methylol group-containing urea compounds, methylol group-containing phenol compounds, alkoxyalkyl group-containing melamine compounds, alkoxyalkyl group-containing benzoguanamine compounds, alkoxyalkyl group-containing urea compounds, alkoxyalkyl group-containing phenol compounds, carboxymethyl group-containing melamine resins, carboxy methyl group-containing benzoguanamine resins, carboxymethyl group-containing urea resins, carboxymethyl group-containing phenol resins, carboxymethyl group-containing melamine compounds, carboxymethyl group-containing benzoguanamine compounds, carboxymethyl group-containing urea compounds, and carboxymethyl group-containing phenol compounds, methylol group-containing phenol compounds, methoxymethyl group-containing melamine compounds, methoxymethyl group-containing phenol compounds, methoxymethyl group-containing glycol-uril compounds, methoxymethyl group-containing urea compounds and acetoxymethyl group-containing phenol compounds. The methoxymethyl group-containing melamine compounds are commercially available as, for example, CYMEL300, CYMEL301, CYMEL303, CYMEL305 (manufactured by Mitsui Cyanamid), the methoxymethyl group-containing glycol-uril compounds are commercially available as, for example, CYMEL117 4 (manufactured by Mitsui Cyanamid), and the methoxymethyl group-containing urea compounds are commercially available as, for example, MX290 (manufactured by Sanwa Chemicals).

In negative-working materials, has also been found that inclusion of the protected materials in photoresists enhances the contrast of the photo generated image as acids that may migrate to areas which have not been exposed to actinic radiation are captured by the protected materials.

It has also been found that inclusion of the protected materials in photoresists enhances the contrast of the photo generated image as acids that may migrate to areas which have not been exposed to actinic radiation are captured by the protected materials.

A photosensitive composition comprising the above compositions of matter may further comprise a solvent to enable spin coating on a semiconductor, other device in process, or other work piece. Suitable solvents include ethers, esters, etheresters, ketones and ketoneesters and, more specifically, ethylene glycol monoalkyl ethers, diethylene glycol dialkyl ethers, propylene glycol monoalkyl ethers, propylene glycol dialkyl ethers, alkyl phenyl ethers such as anisole, acetate esters, hydroxyacetate esters, lactate esters, such as ethyl lactate, methyl lactate, propyl lactate, butyl lactate, ethylene glycol monoalkylether acetates, propylene glycol monoalkylether acetates, alkoxyacetate esters, (non-)cyclic ketones, acetoacetate esters, pyruvate esters and propionate esters. Specific examples of these solvents include ethylene glycol monomethyl ether, ethylene glycol monoethyl ether, ethylene glycol monopropyl ether, ethylene glycol monobutyl ether, diethylene glycol dimethyl ether, diethylene glycol diethyl ether, diethylene glycol dipropyl ether, diethylene glycol dibutyl ether, methylcellosolve acetate, ethyl cellosolve acetate, propylene glycol monomethyletheracetate, propylene glycol monoethyletheracetate, propylene glycol monopropyletheracetate, isopropenyl acetate, isopropenyl propionate, methylethyl ketone, cyclohexanone, 2-heptanone, 3-heptanone, 4-heptanone, 2-hydroxypropionate ethyl, 2-hydroxy-2-methylpropionate ethyl, ethoxy acetate ethyl, hydroxyacetate ethyl, 2-hydroxy-3-methyl methylbutyrate, 3-methoxybutylacetate, 3-methyl-3-methoxybutylacetate, 3-methyl-3-methoxybutyl propionate, 3-methyl-3-methoxybutyl butylate, ethyl acetate, propyl acetate, butyl acetate, methyl acetoacetate, ethyl acetoacetate, methyl 3-methoxypropionate, ethyl 3-methoxy propionate, 3-ethoxy propionate methyl and 3-ethoxy propionate ethyl. The aforementioned solvents may be used independently or as a mixture of two or more types. Furthermore, at least one type of high boiling point solvent such as benzylethyl ether, dihexyl ether, diethylene glycol monomethyl ether, diethylene glycol monoethyl ether, acetonylacetone, isoholon, caproic acid, capric acid, 1-octanol, 1-nonanol, benzyl alcohol, benzyl acetate, ethyl benzoate, diethyl oxalate, diethyl maleate, γ-butyrolactone, ethylene carbonate, propylene carbonate and phenylcellosolve acetate may be added to the aforementioned solvent.

Various additives may be added to the photoresist formulations to provide certain desirable characteristics of the photosensitive composition such as, for example, acid diffusion control agents to retard acid from migrating into unexposed areas of the coating, surfactants and leveling agents to improve coating of substrates, adhesion promoters to improve adhesion of the coating to the substrate and sensitizers to improve the photosensitivity of the photosensitive composition coating during photoexposure, and antifoaming agents and air release agents, as well as other materials well known in the coatings industry.

Some photoresists may additionally encompass one or more optional components or additives in addition to the aforementioned composition of matter, photoacid generators and solvents. Such components include base quenchers. Suitable base quenchers include, but are not limited to, tetramethylammonium hydroxide, triethanolamine, triisopropylamine, N-methylpyrrolidone, 1,8-diazabicyclo[5.4.0]undec-7-ene (DBU), 1,5-diazabicyclo[4.3.0]non-5-ene (DBN), 7-Methyl-1,5,7-triazabicyclo(4.4.0)dec-5-ene, quinuclidine, carboxylate salts such as tetramethylammonium acetate, tetramethylammonium lactate, tetramethylammonium propanoate, and the like.

The photosensitive compositions can be coated onto substrate such as a silicon wafer or a wafer coated with silicon dioxide, aluminium, aluminum oxide, copper, nickel, any of a number of semiconductor materials or nitrides or other substrates well known the semiconductor industry, or a substrate having thereon an organic film, such as, for example, a bottom layer anti-reflective film or the like. The photoresist compositions are applied by such processes as spin coating, curtain coating, slot coating, dip coating, roller coating, blade coating, ultrasonic coating, vapor coating and the like. After coating, the solvent is removed, if applicable, to a level wherein the coating can be properly exposed, and baked and developed, if applicable. In some cases a residual of 5% solvent may remain in the coating while in other cases less than 1% is required. Drying can be accomplished by hot plate heating, convection heating, infrared heating and the like. The coating is then imagewise exposed through a mark containing a desired pattern or flood exposed.

Radiation suitable for the described photosensitive compositions include, for example, ultraviolet rays (UV), such as the bright line spectrum of a mercury lamp (254 nm), a KrF excimer laser (248 nm), and an ArF excimer laser (193 nm), an $F_2$ excimer laser (157 nm), extreme ultraviolet (EUV) such as 13.5 nm from plasma discharge and synchrotron light sources, beyond extreme ultraviolet (BEUV) such as 6.7 nm exposure, X-ray such as synchrotron radiation. Ion beam lithography and charged particle rays such as electron beams may also be used.

Following exposure, the exposed coated substrate may optionally be post exposure baked to enhance the reaction of the generated photoacid, such as, for example, heating from about 30 to about 350° C. for about 10 to about 600 seconds. This may be accomplished by hot plate heating, convection heating, infrared heating and the like. The heating may also be performed by a laser heating processes such as, for example, a $CO_2$ laser pulse heating for about 2 to about 5 milliseconds. Both heating processes may be combined in tandem.

A flood exposure process may be applied after the pattern exposure to aid in further cure. Results have indicated that flood exposure reduces or eliminates pattern collapse after development of the negative-tone resists as well as reduction in line edge roughness. For example, a 532 nm continuous wave laser exposes the previously exposed resist for 1-2 sec followed by wet development. The flood process may or may not be followed by a heating step.

The exposed film is then developed using a suitable a developer. Such developers include organic solvents as well as aqueous solutions such as aqueous alkali solutions known in the art. When an organic solvent is used to remove the unexposed areas generally the solvent is less aggressive than the solvent that was used in preparing the photoresist composition. Examples of aqueous alkali development solution include, for example, at least one type of alkaline compound such alkali metal hydroxides, ammonia water, alkylamines, alkanolamines, heterocyclicamines, tetraalkyl ammonium hydroxides such as tetramethyl ammonium hydroxide, cholines, and 1,8-diazabicyclo[5.4.0]-7-undecan, 1,5-diazabicyclo[4.3.0]-5-nonene at a concentration of about 1 to about 10% by weight, such as, for example, about 2 to about 5% by weight. Water-soluble organic solvents such as methanol and ethanol and surfactants may also be added in suitable amounts to the alkaline aqueous solution, depending on the desired development characteristics and process parameters.

After development a final baking step may be included to further enhance the curing of the now exposed and developed pattern. The heating process may be, for example, from about 30 to about 350° C. for about 10 to about 120 seconds and may be accomplished by hot plate heating, convection heating, infrared heating and the like.

Negative working photosensitive compositions of the current disclosure contain crosslinking material which are protected by acid labile protecting groups. Such crosslinkers include monomer, oligomer and polymers. Such polymers include, for example, phenolic resins, cresol-formaldehyde resins, carboxylic acid containing resins, and hydroxy group containing resins. The reactive portions of these resins are protected by the acid labile protecting groups that are listed above. The composition contain photoacid generators, as listed above, the protected crosslinking materials and other materials which crosslink with the crosslinkers when the reactive portions of the crosslinkers are deprotected. Other materials may also be present in the composition which are generally present in photosensitive coatings, such as, for example, wetting agents, leveling agents, colorants, photosensitizing agents, and the like. Thus the components of the composition are admixed in a solvent and coated onto a substrate and dried to a suitable dryness. The coating is exposed to actinic radiation to convert a portion of the photoacid generator to acid and the acid reacts to deprotect the protected crosslinking materials. The crosslinking materials, by themselves or with the aid of the photogenerated acid, crosslinks the composition. The unexposed areas can now be removed with a developer leaving behind an image.

It has also been found that inclusion of the protected materials in photoresists enhances the contrast of the photo generated image as acids that may migrate to areas which have not been exposed to actinic radiation are captured by the protected materials.

EXAMPLES

Synthesis Example 1

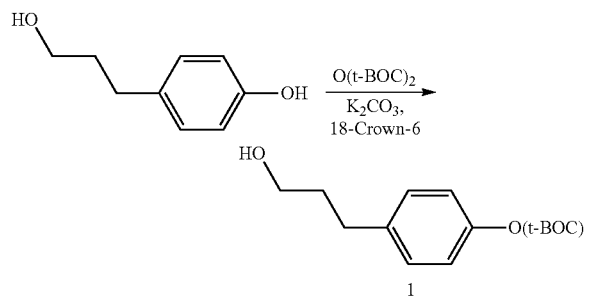

To a 3 L round bottom flask was added 3-(4-hydroxyphenyl)-1-propanol (102.1 g, 670.9 mmol), dichloromethane (760 mL) and di-tert-butyldicarbonate (146.4 g, 670.9 mmol). The mixture was stirred under nitrogen and cooled to 0° C. in an ice bath. Potassium carbonate (250.3 g, 1811.3 mmol) and 18-crown-6 (8.9 g, 33.5 mmol) were added. The resulting mixture was stirred and warmed to room temperature overnight. The crude reaction mixture was evaporated to remove most of the solvent and the residue was purified via flash column chromatography on silica gel with ethyl acetate: Hexane (40%/60%) as eluant. The third fraction was combined together and the solvent removed to give 135.6 g (yield: 80%) of 1 as a yellow oil. The product was characterized by $^1$H NMR.

Synthesis Example 2

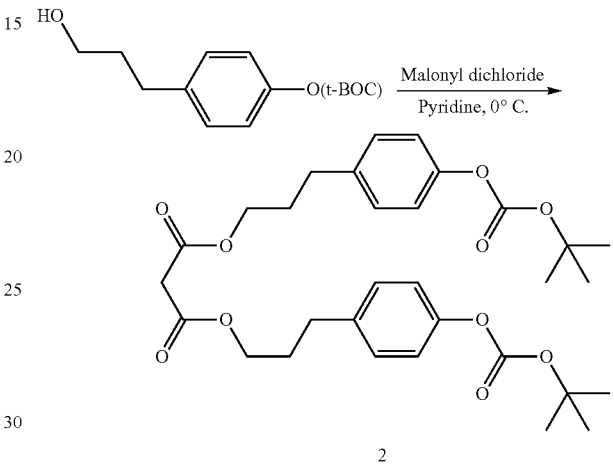

Dichloromethane (2 L) was added to 1 (135.6 g, 537.7 mmol) in a 3 L round bottom flask. To this was added, while stirring, pyridine (56.6 g, 715.1 mmol) and the solution was cooled to 0° C. in an ice bath under nitrogen. Malonyl dichloride (34.8 mL, 357.6 mmol) was added dropwise using an addition funnel. The initially clear solution became dark red upon complete addition of the malonyl dichloride. The mixture was stirred and warmed up to room temperature overnight, by which time it had become dark blue/green in color. The mixture was filtered through a silica gel plug which was rinsed with ethyl acetate. The filtrate was evaporated and the residue was purified via flash column chromatography on silica gel using 25% ethyl acetate/n-hexane as eluant. The fractions were collected and solvent was removed to give 2 as yellow oil (93.1 g, 61% yield). The product was characterized by $^1$H NMR.

Synthesis Example 3

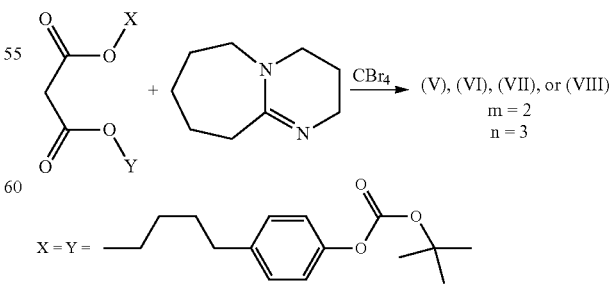

Tetrabromomethane (4.05 g, 12.2 mmol) and 2 (6.3 g, 11.0 mmol) were added to a 500 mL round bottom flask. Toluene (240 mL) was added and the mixture was stirred under nitrogen for 1 hour. 1,8-Diazabicyclo[5.4.0]undec-7-ene (DBU, 7.3 g, 48.2 mmol) was added dropwise. The reaction mixture was stirred under nitrogen for 18 hours and then filtered. The resulting mixture was purified via a silica gel column using toluene, followed by ethyl acetate and then a gradient of 20% to 50% isopropanol/ethyl acetate. The fifth fraction was collected and solvent was removed to give the final product as a light yellow solid (3.4 g). The product was characterized by $^1$H NMR and elemental analysis and $^{13}$C NMR analysis which showed that the most likely product was (V), wherein m=2 and n=3.

Synthesis Example 4

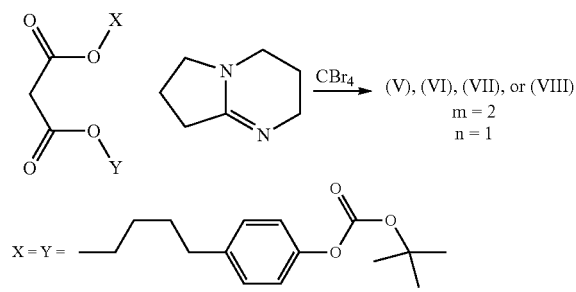

Similar to Synthesis Example 3 except that 1,5-Diazabicyclo(4.3.0)non-5-ene (DBN, 5.95 g, 48.2 mmol) was used. The product was characterized by $^1$H NMR.

The following are hypothetical examples of formulations made with materials disclosed herein.

Composition Example 1

Into 100 mL of propylene glycol monomethyl ether (PGME) is added 0.25 g of the product of Synthesis Example 3, 0.50 g of poly[(o-cresyl glycidyl ether)-co-formaldehyde] and 0.25 g of triphenylsulfonium hexafluoroantimonate. The mixture is stirred for 1 hr at room temperature and filtered through a 20 nm PTFE membrane filter, available from Pall Corporation, of Port Washington N.Y. The composition is applied to a silicon wafer and spin coated at 500 rpm for 5 sec followed by 2000 rpm for 60 sec. The coated wafer is then heated on a hot plate at 75° C. for 5 min to give a film of approximately 25 nm. The coated wafer is then imagewise exposed to synchrotron based EUV light at 13-14 nm wavelength and post exposure baked at 90° C. for 3 min. The unexposed areas are removed by puddle development in a 50:50 blend of monochlorobenzene and isopropyl alcohol for 20 sec followed by an isopropyl alcohol rinse.

Composition Example 2

The formulation and process of Composition Example 1 was used except that the material of synthesis example 4 is used.

Composition Example 3

Into 100 mL of ethyl lactate was added 0.05 g of the product of Synthesis Example 3, 0.50 g of poly[(o-cresyl glycidyl ether)-co-formaldehyde] (Mn=1270) and 0.25 g of triphenylsulfonium hexafluoroantimonate and stirred for 1 hr at room temperature. The composition was applied to a silicon wafer and spin-coated at 500 rpm for 5 sec followed by 1500 rpm for 90 sec. The coated wafer was then heated on a hot plate at 70° C. for 5 min to give a film of approximately 25 nm. The wafer was imagewise exposed to E-beam and post exposure baked at 90° C. for 1 min. The unexposed areas were removed by puddle development in cyclohexanone for 20 sec followed by an isopropyl alcohol rinse. A line dose of 142 pC/cm was applied, given dense lines of 40 nm half pitch. FIG. 3(A) shows the resulting printed features.

Composition Example 4

Composition Example 3 was repeated using poly[(o-cresyl glycidyl ether)-co-formaldehyde] (Mn=870) in place of poly[(o-cresyl glycidyl ether)-co-formaldehyde] (Mn=1270). A line dose of 107 pC/cm was applied, given dense lines of 38 nm half pitch. FIG. 3(B) shows the resulting printed features.

Composition Example 5

Composition Example 3 was repeated adding 0.04 g of triphenylsulfonium nonaflate into resist formulation. A line dose of 117 pC/cm was applied, given dense lines of 38 nm half pitch. FIG. 4(A) shows the resulting printed features.

Composition Example 6

Example 5 was repeated adding 0.008 g of 1,8-Diazabicycloundec-7-ene in the resist formulation. A line dose of 156 pC/cm was applied, given dense lines of 38 nm half pitch. FIG. 4(B) shows the resulting printed features.

Composition Example 7

Into 67.2 mL of ethyl lactate was added 0.05 g of the product of Synthesis Example 4, 0.50 g of poly[(o-cresyl glycidyl ether)-co-formaldehyde] (Mn=870), 0.04 g of triphenylsulfonium trifluoromethane sulfonate, and 0.25 g of triphenylsulfonium hexafluoroantimonate and stirred for 1 hr at room temperature. The composition was applied to a silicon wafer and spin-coated 3000 rpm for 90 sec. The coated wafer was then heated on a hot plate at 105° C. for 5 min to give a film of approximately 25 nm. The wafer was imagewise exposed using EUV light having a wavelength of about 13.4 nm, at 88 mJ/cm$^2$ dose to mask (dose to wafer estimate 8.8 mJ/cm$^2$), and post exposure baked at 90° C. for 3 min. The unexposed areas were removed by puddle development in cyclohexanone for 30 sec followed by an isopropyl alcohol rinse, producing lines of 14 nm half pitch. FIG. 5 shows the resulting printed features.

Although the present invention has been shown and described with reference to particular examples, various changes and modifications which are obvious to persons skilled in the art to which the invention pertains are deemed to lie within the spirit, scope and contemplation of the subject matter set forth in the appended claims.

What is claimed is:
1. A photosensitive composition comprising:
a. At least one ester, having a structure chosen from (I), (II), (III) or (IV);

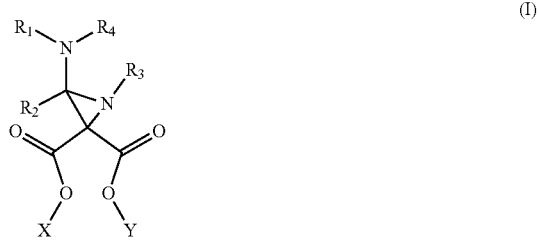

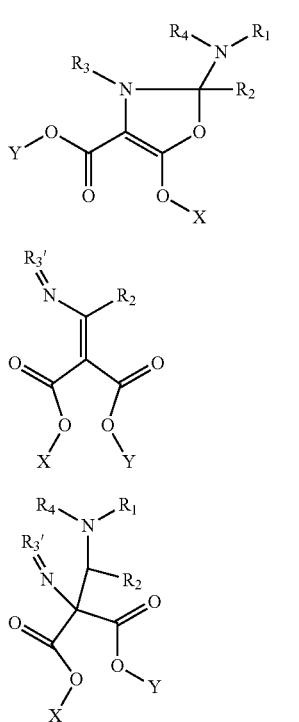

b. at least one photo acid generator;
c. at least one crosslinker; and
d. at least one solvent;
wherein X and Y are the same or different, wherein at least one of X and Y comprises an acid labile group, wherein R1 is a saturated or unsaturated group having from 1-4 carbon atoms, R2 is chosen from hydrogen or a saturated or unsaturated group having from 1-4 carbon atoms, R3 is a saturated or unsaturated group having from 1-4 carbon atoms, and R4 is a saturated or unsaturated group having from 1-4 carbon atoms.

2. The photosensitive composition of claim 1, wherein at least one of X or Y comprises

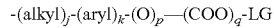

wherein j, k, p, and q take the values in the following table:

| -alkyl- j | -aryl- k | —O— p | —COO— q |
|---|---|---|---|
| 1 | 1 | 1 | 1 |
| 1 | 1 | 0 | 1 |
| 1 | 1 | 1 | 0 |
| 1 | 0 | 0 | 1 |
| 1 | 0 | 1 | 0 |
| 0 | 1 | 1 | 1 |
| 0 | 1 | 0 | 1 |
| 0 | 1 | 1 | 0 |
| 0 | 0 | 0 | 1 | wherein alkyl is a branched or unbranched, substituted or unsubstituted divalent alkyl chain of 1-16 carbon atoms having 0-16 heteroatoms substituted into the chain, aryl is a substituted or unsubstituted divalent phenyl group, divalent heteroaromatic group, or divalent fused aromatic or fused heteroaromatic group, and wherein LG is a leaving group.

3. The photosensitive composition of claim 2, wherein LG is a tertiary alkyl or tertiary cycloalkyl group, an allicyclic group, a ketal or cyclic aliphatic ketal, or an acetal.

4. The photosensitive composition of claim 2, wherein the leaving group is a tert-butyl group, a tert-pentyl group, a 2,3-dimethylbutan-2-yl group, a 2,3,3-trimethylbutan-2-yl group, a 2,3-dimethylpentan-3-yl group, a 2-methylbicyclo[2.2.1]heptan-2-yl group, a bicyclo[2.2.1]heptan-2-yl group, a 1-methylcyclopentyl group, a 1-ethylcyclopentyl group, a 1-methylcyclohexyl group, a 1-ethylcyclohexyl group, a 2-methyladamantyl group or a 2-ethyladamantyl group.

5. The photosensitive composition of claim 4, wherein the at least one photoacid generator is chosen from a sulfonium salt, an iodonium salt, a sulfone imide, a halogen-containing compound, a sulfone compound, an ester sulfonate compound, a diazomethane compound, a dicarboximidyl sulfonic acid ester, an ylideneaminooxy sulfonic acid ester, a sulfanyl-diazomethane, or a mixture thereof.

6. The photosensitive composition of claim 5, wherein the at least one photoacid generator comprises a triphenylsulfonium salt or a bis(4-tert-butylphenyl)iodonium salt.

7. The photosensitive composition of claim 4, wherein the at least one crosslinker comprises an acid sensitive monomer or polymer.

8. The photosensitive composition of claim 4, wherein the crosslinker comprises at least one of a glycidyl ether, glycidyl ester, glycidyl amine, a methoxymethyl group, an ethoxy methyl group, a butoxymethyl group, a benzyloxymethyl group, dimethylamino methyl group, diethylamino methyl group, a dibutoxymethyl group, a dimethylol amino methyl group, diethylol amino methyl group, a dibutylol amino methyl group, a morpholino methyl group, acetoxymethyl group, benzyloxy methyl group, formyl group, acetyl group, vinyl group or an isopropenyl group.

9. The photoresist composition of claim 8, wherein the crosslinker comprises one or more glycidyl ether groups attached to a novolac resin.

10. The photosensitive composition of claim 1, wherein the solvent comprises an ester, an ether, an ether-ester, a hydroxy ester, a hydroxy ether, a ketone, a keto-ester, a hydrocarbon, an aromatic compound, a halogenated solvent, an alkyl-aryl ether or a combination thereof.

11. A photosensitive composition comprising:
a. At least one ester, having a structure chosen from (V), (VI), (VII) or (VIII);

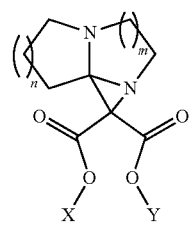

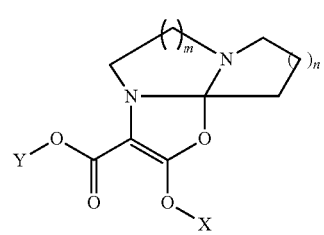

-continued

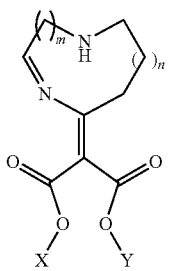
(VII)

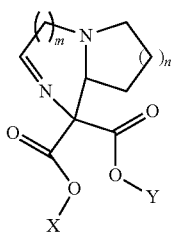
(VIII)

b. at least one photo acid generator; and
c. at least one crosslinker;
wherein m=1-4, n=1-4, and wherein X and Y are the same or different, wherein at least one of X and Y comprises an acid labile group.

12. The photosensitive composition of claim 11, wherein at least one of X or Y comprises

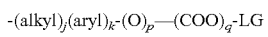

wherein j, k, p, and q take the values in the following table:

| -alkyl- j | -aryl- k | —O— p | —COO— q |
|---|---|---|---|
| 1 | 1 | 1 | 1 |
| 1 | 1 | 0 | 1 |
| 1 | 1 | 1 | 0 |
| 1 | 0 | 0 | 1 |
| 1 | 0 | 1 | 0 |
| 0 | 1 | 1 | 1 |
| 0 | 1 | 0 | 1 |
| 0 | 1 | 1 | 0 |
| 0 | 0 | 0 | 1 | wherein alkyl is a branched or unbranched, substituted or unsubstituted divalent alkyl chain of 1-16 carbon atoms having 0-16 heteroatoms substituted into the chain, aryl is a substituted or unsubstituted divalent phenyl group, divalent heteroaromatic group, or divalent fused aromatic or fused heteroaromatic group, and wherein LG is a leaving group.

13. The photosensitive composition of claim 12, wherein LG is a tertiary alkyl or tertiary cycloalkyl group, an allicyclic group, a ketal or cyclic aliphatic ketal, or an acetal.

14. The photosensitive composition of claim 12, wherein m=2, n=3, and LG is a tert-butyl carbonate group.

15. The photosensitive composition of claim 13, wherein LG is a tert-butyl group, a tert-pentyl group, a 2,3-dimethylbutan-2-yl group, a 2,3,3-trimethylbutan-2-yl group, a 2,3-dimethylpentan-3-yl group, a 2-methylbicyclo[2.2.1]heptan-2-yl group, a bicyclo[2.2.1]heptan-2-yl group, a 1-methylcyclopentyl group, a 1-ethylcyclopentyl group, a 1-methylcyclohexyl group, a 1-ethylcyclohexyl group, a 2-methyladamantyl group or a 2-ethyladamantyl group.

16. The photosensitive composition of claim 15, wherein the at least one photoacid generator is chosen from a sulfonium salt, an iodonium salt, a sulfone imide, a halogen-containing compound, a sulfone compound, an ester sulfonate compound, a diazomethane compound, a dicarboximidyl sulfonic acid ester, an ylideneaminooxy sulfonic acid ester, a sulfanyldiazomethane, or a mixture thereof.

17. The photosensitive composition of claim 16, wherein the at least one photoacid generator comprises a triphenylsulfonium salt or a bis(4-tert-butylphenyl)iodonium salt.

18. The photosensitive composition of claim 12, wherein the at least one crosslinker comprises an acid sensitive monomer or polymer.

19. The photosensitive composition of claim 12, wherein the crosslinker comprises at least one of a glycidyl ether, glycidyl ester, glycidyl amine, a methoxymethyl group, an ethoxy methyl group, a butoxymethyl group, a benzyloxymethyl group, dimethylamino methyl group, diethylamino methyl group, a dibutoxymethyl group, a dimethylol amino methyl group, diethylol amino methyl group, a dibutylol amino methyl group, a morpholino methyl group, acetoxymethyl group, benzyloxy methyl group, formyl group, acetyl group, vinyl group or an isopropenyl group.

20. The photosensitive composition of claim 12, wherein the crosslinker comprises one or more glycidyl ether groups attached to a novolac resin.

21. The photosensitive composition of claim 12, further comprising a solvent, wherein the solvent comprises an ester, an ether, an ether-ester, a hydroxy ester, a hydroxy ether, a ketone, a keto-ester, a hydrocarbon, an aromatic compound, a halogenated solvent, an alkyl-aryl ether or a combination thereof.

* * * * *